(12) United States Patent
Inglese et al.

(10) Patent No.: US 12,274,574 B2
(45) Date of Patent: Apr. 15, 2025

(54) INTRAORAL X-RAY SYSTEM

(71) Applicant: CARESTREAM DENTAL LLC, Atlanta, GA (US)

(72) Inventors: Jean-Marc Inglese, Bussy-Saint-Georges (FR); David Roudergues, Courbevoie (FR); Arnaud Capri, Marne la Vallee (FR); Vincent Loustauneau, Fontenay sous Bois (FR); Subramanyan Krishnamoorthy, Penfield, NY (US)

( * ) Notice: Subject to any disclaimer, the term of this patent is extended or adjusted under 35 U.S.C. 154(b) by 112 days.

(21) Appl. No.: 18/215,460

(22) Filed: Jun. 28, 2023

(65) Prior Publication Data

US 2023/0337993 A1    Oct. 26, 2023

Related U.S. Application Data

(63) Continuation-in-part of application No. 17/792,000, filed as application No. PCT/US2020/067244 on Dec. 29, 2020, and a continuation of application No. PCT/US2021/039847, filed on Jun. 30, 2021.

(60) Provisional application No. 62/956,732, filed on Jan. 3, 2020.

(51) Int. Cl.
*A61B 6/51* (2024.01)
*A61B 6/00* (2006.01)

(52) U.S. Cl.
CPC ............ *A61B 6/512* (2024.01); *A61B 6/4458* (2013.01); *A61B 6/4476* (2013.01); *A61B 6/547* (2013.01)

(58) Field of Classification Search
CPC ..... A61B 6/512; A61B 6/4458; A61B 6/4476; A61B 6/547; A61B 6/51; A61B 6/584
See application file for complete search history.

(56) References Cited

U.S. PATENT DOCUMENTS 5,113,424 A * 5/1992 Burdea .................... A61B 6/08
378/170

* cited by examiner

*Primary Examiner* — Kiho Kim

(57) ABSTRACT

The present invention provides an intraoral X-ray system comprising:
an X-ray source located in an environment;
a robotic arm comprising an actuatable scissor arm, the robotic arm having a first end configured to be attached to a mounting and a second end attached to the X-ray source, at least one of the first and the second ends comprising a rotatable actuatable joint;
a position sensor to determine variation of position and/or orientation of the environment with respect to the X-ray source and variation of position and/or orientation of a mobile X-ray sensor with respect to the X-ray source; and
a driving unit actuating the robotic arm as a function of the determined variation of position and/or orientation to control the position and/or orientation of the X-ray source with respect to a predetermined position and/or orientation of the X-ray source.

20 Claims, 4 Drawing Sheets

INTRAORAL X-RAY SYSTEM

FIELD OF THE INVENTION

The present invention relates to the field of X-ray systems for the health care industry. Particularly, but not exclusively, the invention relates to intraoral X-ray systems used in the dental industry.

BACKGROUND OF THE INVENTION

Intraoral X-ray systems are generally used to provide two-dimensional (2D) images of a patient's teeth. When a practitioner uses an intraoral X-ray system with a patient, an intraoral sensor is placed inside the patient's mouth behind a tooth or teeth to be imaged and the system's external X-ray source is brought near the patient's face into the vicinity of the area to be imaged.

The X-ray sources of such intraoral X-ray systems are usually mounted on an articulated arm with the X-ray source being attached at a first end of the articulated arm. A second end of the articulated arm may be attached to a wall, on a dental chairside, or on a standalone base. If the second end of the articulated arm is attached to a wall, the wall must be stable, flat, and perpendicular to the floor of the practitioner's office. Because not all walls are stable, flat, and perpendicular to a floor, installation of the articulated arm to a wall can be challenging and time-consuming. If the articulated arm is attached to a dental chairside or standalone base, additional room is required around the dental chair which is often not available in many practitioner's offices.

Regardless of where the articulated arm is affixed, the X-ray source is often heavy and, therefore, the articulated arm includes springs and cables to maintain the X-ray source stable while an X-ray image is taken of the patient's tooth or teeth. Unfortunately, even with the springs and cables, drift instability may occur during X-ray imaging, causing blurring and other possible difficulties that affect image quality. And, if the wall is not sufficiently flat, stable, and perpendicular to the floor, the instability may be made worse.

Additionally, because the articulated arm is affixed to a wall, dental chairside, or standalone base, the X-ray source is generally limited to being used only in a particular examination room, requiring the practitioner to equip his/her office with multiple X-ray sources in different examination rooms or requiring patients to be shuttled around the office between examination rooms for X-ray imaging purposes. The practitioner's investment in intraoral X-ray imaging systems could be reduced if the X-ray source were mobile. Also, with a mobile X-ray source, tomosynthesis examinations could be conducted in various examination rooms at minimal cost to the practitioner.

In addition, as previously mentioned, the practitioner moves the X-ray source near the patient's face in order to perform the X-ray imaging, but it can sometimes be difficult for the practitioner to do so if the patient is moving. Further, if the patient moves slightly before or during X-ray imaging, the image quality will likely be adversely affected. If a satisfactory X-ray image is not obtained, the practitioner must take another X-ray image, thereby increasing the X-ray dose to the patient.

Therefore, there is a need in the industry for an intraoral X-ray system that is simpler to install and use, that improves positioning of the X-ray source near the patient's face, that produces quality X-ray images, and that solves these and other problems, difficulties and shortcomings of current systems.

SUMMARY OF THE INVENTION

Broadly described, the present invention comprises an intraoral X-ray system, including apparatuses and methods, for producing dental X-ray images. Advantageously, the intraoral X-ray system of the present invention makes installation simpler on a wall of a practitioner's office because the movable components of the intraoral X-ray system can be moved to compensate for defects in the flatness of the wall or for the wall not being sufficiently perpendicular to the floor. Also, due at least in part to its monitoring and compensation capabilities, the intraoral X-ray system can compensate for drift in the position of the X-ray source before and during X-ray imaging, thereby avoiding the need for taking additional X-ray images and exposing the patient unnecessarily to extra X-ray dose. The intraoral X-ray system can also, as described herein, compensate automatically for patient movements before and during X-ray imaging. And, because the X-ray source may be precisely moved under the control of a data/signal processing unit along a pre-determined trajectory, the intraoral X-ray system may be used to perform computed tomosynthesis examinations of a patient. Further, because the X-ray source and robotic arm may be designed for the X-ray source to be attachable/detachable from the robotic arm and remainder of the intraoral X-ray system, no violent, unstable reaction occurs when the X-ray source is detached and removed from connection with the robotic arm. Instead, the data/signal processing unit may detect the variation in weight at the second end of the robotic arm due to removal of the X-ray source and operates the robotic arm and other movable components of the intraoral X-ray system to automatically compensate for the variation in weight in a safe and predictable manner.

According to a particular aspect of the disclosure, there is provided an intraoral X-ray system comprising:
- an X-ray source located in an environment;
- a robotic arm comprising an actuatable scissor arm, the robotic arm having a first end configured to be attached to a mounting and a second end attached to the X-ray source, at least one of the first and the second end comprising a rotatable actuatable joint;
- a position sensor to determine variation of position and/or orientation of the environment with respect to the X-ray source and variation of position and/or orientation of a mobile X-ray sensor with respect to the X-ray source; and
- a driving unit actuating the robotic arm as a function of the determined variation of position and/or orientation to control the position and/or orientation of the X-ray source with respect to a predetermined position and/or orientation of the X-ray source.

The intraoral X-ray system according to the invention provides simplified installation, operation, and maintenance. In particular, the intraoral X-ray system according to the invention does not require specific characteristics of the mounting on which it is mounted other than its robustness.

In an embodiment, the variation of position and/or orientation of the environment with respect to the X-ray source and the variation of position and/or orientation of the mobile X-ray sensor with respect to the X-ray source are determined within a same reference frame associated with the X-ray source to simplify and speed up processing.

In an embodiment, the driving unit is configured to control the actuatable scissor arm and/or at least one of the rotatable actuatable joints.

In an embodiment, the driving unit is configured to lock the actuatable scissor arm and/or at least one of the rotatable actuatable joint in a predetermined position, so as to facilitate the assembly and disassembly of the X-ray source and to improve storage. Accordingly, the practitioner may switch the robotic arm to a locked configuration which is easily achieved due to the robotic arm and other movable components of the intraoral X-ray system. The robotic arm is then secured whatever the position of the X-ray sensor.

In an embodiment, the position sensor comprises a first position sensor for determining variation of position and/or orientation of the environment with respect to the X-ray source and a second position sensor for determining variation of position and/or orientation of a mobile X-ray sensor with respect to the X-ray source, each of the first and the second position sensor comprising at least one of a gyroscope, an accelerometer, and a localizer for locating a predetermined member.

In an embodiment, the localizer comprises a radio receiver and a computing unit for locating at least one radio emitter.

In an embodiment, each of the rotatable actuatable joints enables a rotation about one axis, two axes, or three axes.

In an embodiment, the driving unit is configured to control a movement of the X-ray source according to a predetermined path with respect to the X-ray sensor.

In an embodiment, the X-ray source is detachable from the second end of the robotic arm.

In an embodiment, the X-ray source is controlled and powered through a connector comprising a first part belonging to the robotic arm and a second part belonging to the X-ray source, the second part of the connector making it possible to connect an external power module to the X-ray source to provide power to the X-ray source.

In an embodiment, the X-ray source comprises a display.

In an embodiment, the system further comprises the X-ray sensor.

In an embodiment, the system further comprises at least one radio emitter carried by the X-ray sensor.

In an embodiment, the localizer comprises at least two cameras and a computing unit configured for locating a spatial arrangement of visual markers, wherein the visual markers are located on the X-ray sensor and are in the field of view of the cameras.

In an embodiment, the driving unit is configured to actuate the robotic arm to control the position and/or orientation of the X-ray source with respect to the X-ray sensor during one of an approach stage prior to acquisition, an acquisition stage, or a storage stage further to acquisition.

In an embodiment, the system comprises an obstacle detector, the driving unit being configured for stopping movement of the X-ray source upon detection of an obstacle on a trajectory of the X-ray source.

According to another particular aspect of the disclosure, there is provided a method for controlling an X-ray system described above, the method comprising, obtaining a variation of a position and/or an orientation of the environment where the X-ray source is located with respect to the X-ray source and a variation of a position and/or an orientation of the X-ray sensor with respect to the X-ray source;

determining in real-time a movement of the X-ray source to compensate for the obtained variations of position and/or orientation;

actuating the robotic arm to move the X-ray source as a function of the determined movement.

The method according to the invention provides simplified installation, operation, and maintenance of the intraoral X-ray system.

According to a particular embodiment, determining in real-time the movement of the X-ray source comprises determining in real-time a compensation movement of the X-ray source to compensate for the obtained variations of position and/or orientation of the X-ray source and/or of the X-ray sensor and obtaining a position to reach along a predetermined path to be followed by the X-ray source with respect to the X-ray sensor, the determined movement of the X-ray source resulting from the combination of the compensation movement and of the obtained position. At least parts of the methods according to the invention may be computer implemented. Accordingly, the present invention may take the form of an entirely hardware embodiment or an embodiment combining software and hardware aspects that may all generally be referred to herein as a "circuit", "module" or "system". Furthermore, parts of the present invention may take the form of a computer program product embodied in any tangible medium of expression having computer usable program code embodied in the medium.

Since parts of the present invention can be implemented in software, parts of the present invention can be embodied as computer readable code for provision to a programmable apparatus on any suitable carrier medium. A tangible carrier medium may comprise a storage medium such as a floppy disk, a CD-ROM, a hard disk drive, a magnetic tape device or a solid state memory device and the like. A transient carrier medium may include a signal such as an electrical signal, an electronic signal, an optical signal, an acoustic signal, a magnetic signal or an electromagnetic signal, e.g. a microwave or RF signal.

BRIEF DESCRIPTION OF THE DRAWINGS

Embodiments of the invention will now be described, by way of example only, and with reference to the following drawings in which.

DETAILED DESCRIPTION OF THE INVENTION

According to some embodiments of the invention, an intraoral X-ray system comprises a position sensor to determine the relative position and/or orientation of an X-ray source of the intraoral X-ray system with respect to an X-ray sensor and to determine a displacement of the X-ray source of the intraoral X-ray system. In addition, the X-ray system comprises a robotic arm at least partially controlled by a driving unit as a function of outputs of the position sensor. Still according to some embodiments of the invention, the X-ray source is attached to the robotic arm so that the position and/or the orientation of the X-ray source remains almost immobile with respect to the X-ray sensor.

Figure 1:
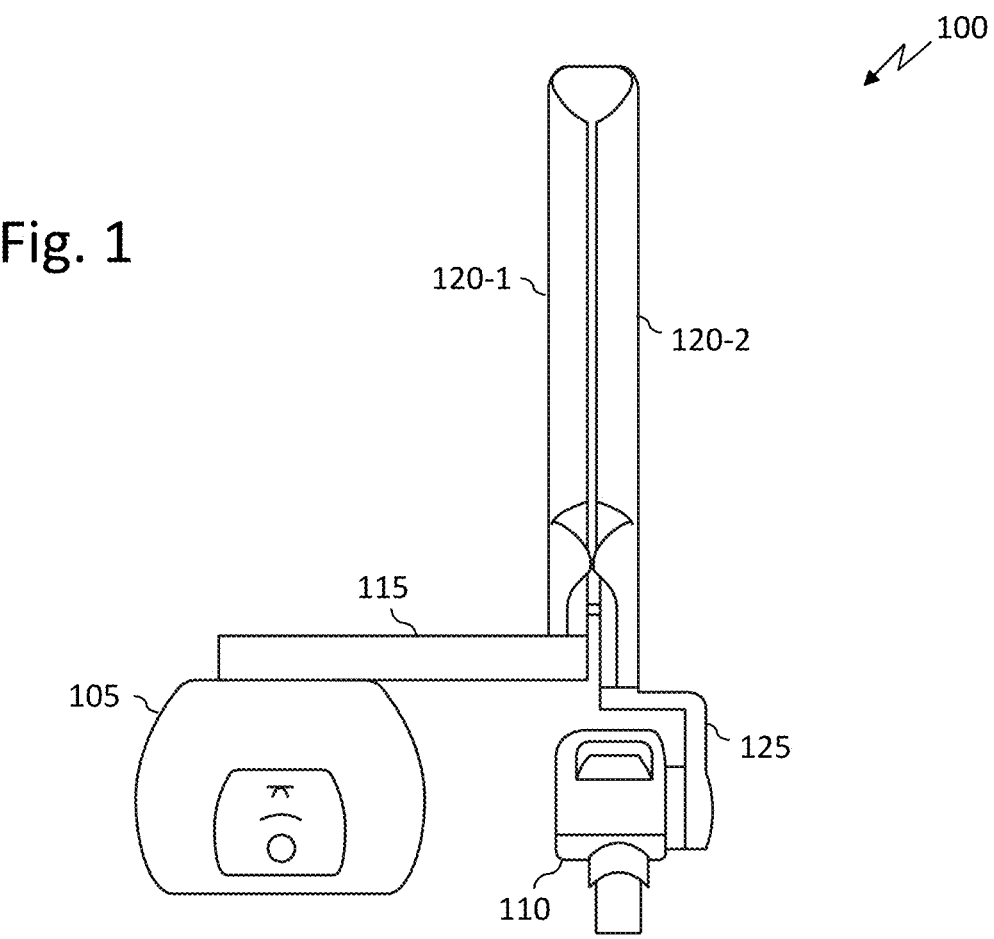
FIG. 1 illustrates a first example of an intraoral X-ray system, in a folded state, in which some embodiments of the invention can be implemented.

FIG. 1 illustrates a first example of an intraoral X-ray system, in a folded state, in which some embodiments of the invention can be implemented.

According to this example, the X-ray system, referenced 100, is mounted on a wall by means of a wall framework 105 that may comprise part of the electronics of the X-ray system, for example a control timer unit and an X-ray exposure button (not represented). The X-ray source, referenced 110, is attached to wall framework 105 via a robotic arm comprising several mobile members, for example an optional extension arm referenced 115, an actuatable scissor arm comprising members 120-1 and 120-2, generically referenced 120, and an optional adapter 125. According to the illustrated example, extension arm 115 is mobile in a horizontal plane, about a vertical axis extending from wall framework 105. For example, extension arm 115 may be connected to wall framework 105 via a rotatable and operable linkage member. Still according to this example, scissor arm 120 is mobile about a vertical axis extending from extension arm 115, at the opposite end from the one around which it is attached to wall framework 105. Again, scissor arm 120 may be connected to extension arm 115 via a rotatable and operable linkage member. In addition, the ends of scissor arm 120 are movable relative to each other in a horizontal direction to bring them closer or further apart. Still according to this example, X-ray source 110 is attached at the opposite end of the scissor arm, with the help of adapter 125 which allows a rotational movement about a vertical axis extending from the end of the scissor arm and about a horizontal axis.

Of course, other configurations are possible.

According to some embodiments, each movement or some of the movements of members of intraoral X-ray system 100 are motorized so that the position and the orientation of X-ray source 110 may be controlled by a processing unit such as a computer. For the sake of illustration, the actuators used to move these members may comprise one or several stepper motors and one or several hydraulic cylinders.

Figure 2:
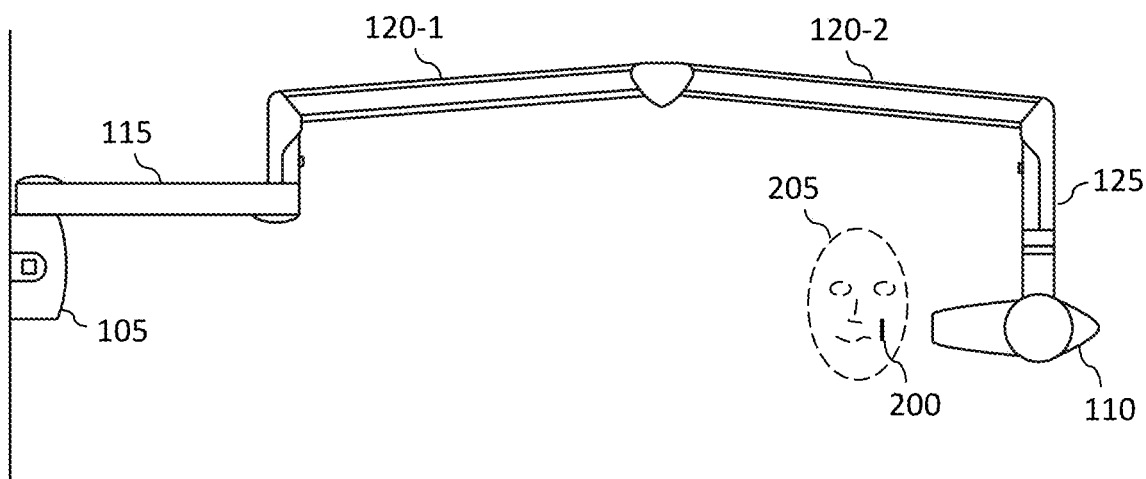
FIG. 2 illustrates the intraoral X-ray system of FIG. 1 in an unfolded state.

FIG. 2 illustrates the intraoral X-ray system of FIG. 1 in an unfolded state. As can be seen, such an unfolded state makes it possible to position X-ray source 110 in front of an X-ray sensor, for example X-ray sensor 200 that is placed in the mouth of patient 205.

Figure 3:
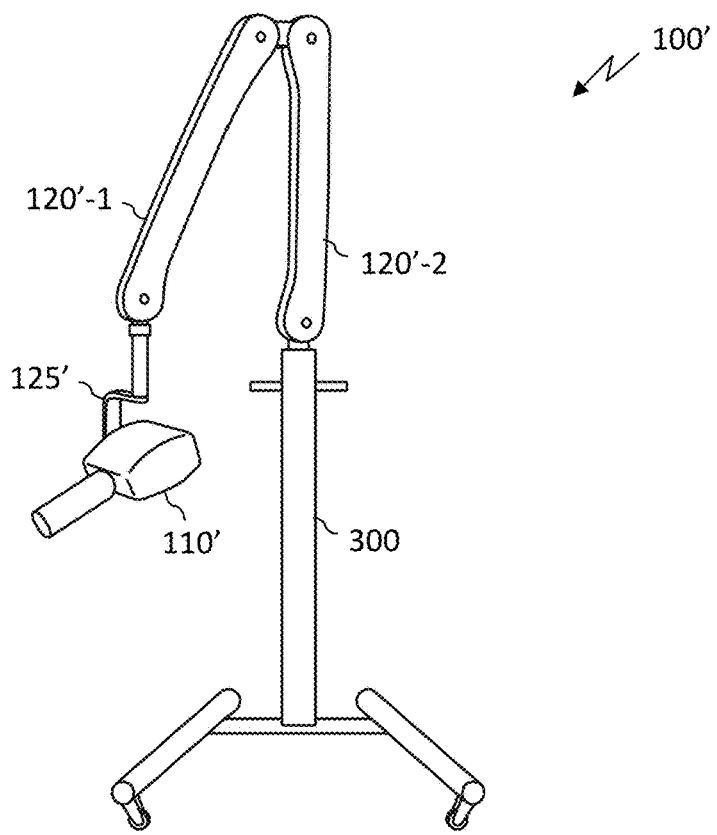
FIG. 3 illustrates a second example of an intraoral X-ray system in which some embodiments of the invention can be implemented.

FIG. 3 illustrates a second example of an intraoral X-ray system in which some embodiments of the invention can be implemented. According to this example, intraoral X-ray system 100' is mobile and comprises a mobile base to which is attached an actuatable scissor arm 120'. According to the illustrated example, scissor arm 120' is mobile about a vertical axis extending from mobile base 300. Scissor arm 120' may be connected to mobile base 300 via a rotatable and operable linkage member. Like the ends of scissor arm 120, the ends of scissor arm 120' are movable relative to each other in a horizontal direction to bring them closer or further apart and X-ray source 110' is attached at the opposite end of the scissor arm, with the help of adapter 125' which allows a rotational movement according to a vertical axis extending from the end of the scissor arm and according to a horizontal axis.

Again, other configurations are possible.

Likewise, each movement or some of the movements of members of intraoral X-ray system 100' are motorized so that the position and the orientation of X-ray source 110' may be controlled by a processing unit such as a computer. Again, the actuators used to move these members may comprise one or several stepper motors and one or several hydraulic cylinders.

X-ray source 110 or 110' may comprise a conventional thermionic X-ray tube source or a cold-cathode X-ray source such as one that includes carbon nanotubes that reduce its weight and simplify the design of the robotic arm. The X-ray source may be controlled and powered through a connector comprising a first part belonging to the robotic arm and a second part belonging to the X-ray source, and if the X-ray source is made attachable to/detachable from the robotic arm, the second part of the connector can support the attachment of a power module for example such as one that includes batteries or supercapacitors. Such a power module may be included in a handle to which the X-ray source may be attached after being detached from the robotic arm. Optionally, the X-ray source may comprise a display suitable for displaying exposure parameters and/or remaining power in the power module.

According to particular embodiments of the invention, the robotic arm may be operated and moved during X-ray computed tomography imaging to move the X-ray source along a desired path, i.e. a desired trajectory and orientation with respect to the X-ray sensor.

According to particular embodiments of the invention, the robotic arm may be operated before irradiating the X-ray sensor in order to position the X-ray source at a desired position with respect to the X-ray sensor. Similarly, the robotic arm may be operated after irradiating the X-ray sensor (or at any time) in order to position the X-ray source in a storage position.

Still according to particular embodiments of the invention, the driving unit is configured to lock the actuatable scissor arm and/or at least one rotatable actuatable joint in a predetermined position making it possible to detach the X-ray source from the robotic arm. Such a position making it possible to detach the X-ray source from the robotic arm may be the same position as the storage position or may be a different position.

Still according to particular embodiments, the X-ray source and/or the robotic arm comprises an obstacle detector such as an optical proximity detector so as to avoid collision of the X-ray source with an object when the X-ray source is moved.

Figure 4:
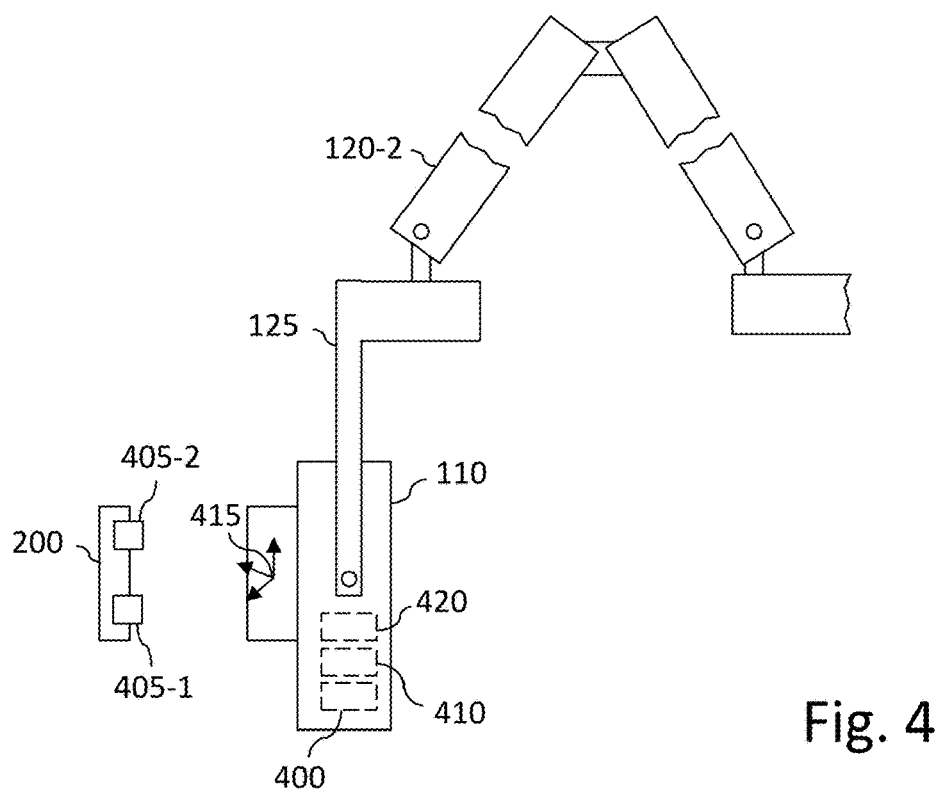
FIG. 4 is a schematic block diagram of a portion of an intraoral X-ray system such as the one illustrated in FIGS. 1 and 2 or in FIG. 3, making it possible to control the position and/or orientation of an X-ray source according to some embodiments of the invention, so that it remains almost immobile with respect to the X-ray sensor.

FIG. 4 is a schematic block diagram of a portion of an intraoral X-ray system such as the one illustrated in FIGS. 1 and 2 or in FIG. 3, making it possible to control the position and/or orientation of an X-ray source according to some embodiments of the invention, so that it remains almost immobile with respect to the X-ray sensor.

For the sake of clarity, reference is made only to FIGS. 1 and 2. However, it must be understood that the description of FIG. 4 also applies to the X-ray system of FIG. 3 and to any similar X-ray system.

As illustrated, X-ray source 110 is attached to adapter 125 via a rotatable and operable linkage member enabling X-ray source 110 to rotate around a horizontal axis. In turn, adapter 125 is attached to scissor arm member 120-2 via a rotatable and operable linkage member enabling adapter to rotate around a vertical axis. The robotic may comprise other actuatable members such as rotatable actuatable joints.

According to the illustrated example, X-ray source 110 comprises (or carries) a first position sensor (or a first portion of a position sensor), referenced 400, to determine the relative position and/or orientation of X-ray sensor 200 with respect to X-ray source 110. Therefore, by determining a change in the position and/or orientation of X-ray sensor 200 with respect to X-ray source 110, it is possible to control the robotic arm comprising, in the illustrated example, scissor arm 120 and adapter 125 so as to correct the position and/or orientation of X-ray source 110 with respect to X-ray sensor 200 in order for X-ray source 110 to remain almost immobile with respect to X-ray sensor 200.

For the sake of illustration, the first position sensor may comprise one or several radio receivers, such as radio receiver 400, to locate one or several radio emitters associated with the X-ray sensor, for example radio emitters 405-1 and 405-2 attached to X-ray sensor 200. By measuring radio signals emitted by radio emitters, a processing unit associated with a radio receiver is able to determine the relative position of the radio emitters and thus, of an X-ray sensor associated with these radio emitters. An example of such a first position sensor is disclosed in Patent Applications No. US 2009/0060145 and No. WO 2012/166262.

Other types of position sensor may be used, such as position trackers used in Virtual Reality systems. For the sake of illustration, such a position tracker may be an optical position tracking system comprising an arrangement of fixed visual markers associated with two video cameras located on the X-ray source. In this embodiment, the fixed visual markers are attached to the X-ray sensor and are located in the field of view of each of the two video cameras when the X-ray sensor is placed inside the mouth of the patient. Knowing the spatial configuration of the visual markers and the spatial configuration of the two cameras, the position and the orientation of the X-ray sensor can be determined. As an alternative of these visual markers, a tag such as a QR code, comprising a rotationally invariant pattern, could be used. In addition, instead of measuring a position and/or an orientation, it is possible to measure a movement.

Still according to the illustrated example, X-ray source 110 further comprises (or carries) a second position sensor (or a second portion of a position sensor), referenced 410, to determine a displacement of the X-ray source with respect to a reference frame associated with the environment wherein is located the X-ray system (e.g. a reference frame associated with a wall of the room where the X-ray source is located). According to some particular embodiments and in order to simplify further calculations (i.e. to avoid a change of reference frame), the X-ray source is considered as fixed and the environment in which the X-ray source is located is considered as mobile. In such cases, the second position sensor provides the displacement of the environment with respect to the X-ray source.

Therefore, by determining a displacement of the X-ray source with respect to a reference frame associated with the environment wherein is located the X-ray system or a movement of the environment with respect to X-ray source 110, it is possible to control the robotic arm comprising, in the illustrated example, scissor arm 120 and adapter 125 so as to correct the position and/or orientation of X-ray source 110 with respect to the environment in order for X-ray source 110 to remain almost immobile with respect to environment, that is to say to detect drift of the X-ray source position and to compensate for the drift automatically in real time.

For the sake of illustration, the second position sensor may comprise one or several accelerometers and/or one or several gyroscopes, for example accelerometers and gyroscopes embedded within integrated circuits such as the ones provided in a large number of smartphones. Other types of position sensor may be used. In addition, instead of measuring a movement, it is possible to measure a position and/or an orientation.

Combining the compensation movement to be applied to the X-ray source 110 as determined by the output of the first position sensor and the compensation movement to be applied to the X-ray source 110 as determined by the output of the second position sensor makes it possible to improve the quality of the images obtained from data issued by the X-ray sensor. To facilitate the combination of these compensation movements, the same reference frame (for example reference frame 415) is preferably used to determine the relative movement of the X-ray sensor with respect to the X-ray source and to determine the relative movement of the environment with respect to the X-ray source.

Combining the outputs of the first and second position sensors (which may collectively be referred to as a or the "position sensor") to control the robotic arm, that is to say to determine the control commands to be sent to actuators of the robotic arm to compensate for the drift of the X-ray source and the movement of the X-ray sensor, may be done in a processing unit, for example in driving unit 420 that is embedded within the X-ray source. According to a particular embodiment, driving unit 420 comprises the processing unit used to locate one or several radio emitters as described above.

According to other embodiments, the driving unit is external from the X-ray source. In such a case, the data issued from the first and second position sensors and the control commands transmitted to actuators of the robotic arm may be sent according to a standard wireless protocol (e.g. using Bluetooth or WiFi protocol, Bluetooth and WiFi are trademarks) or using wires.

Figure 5:
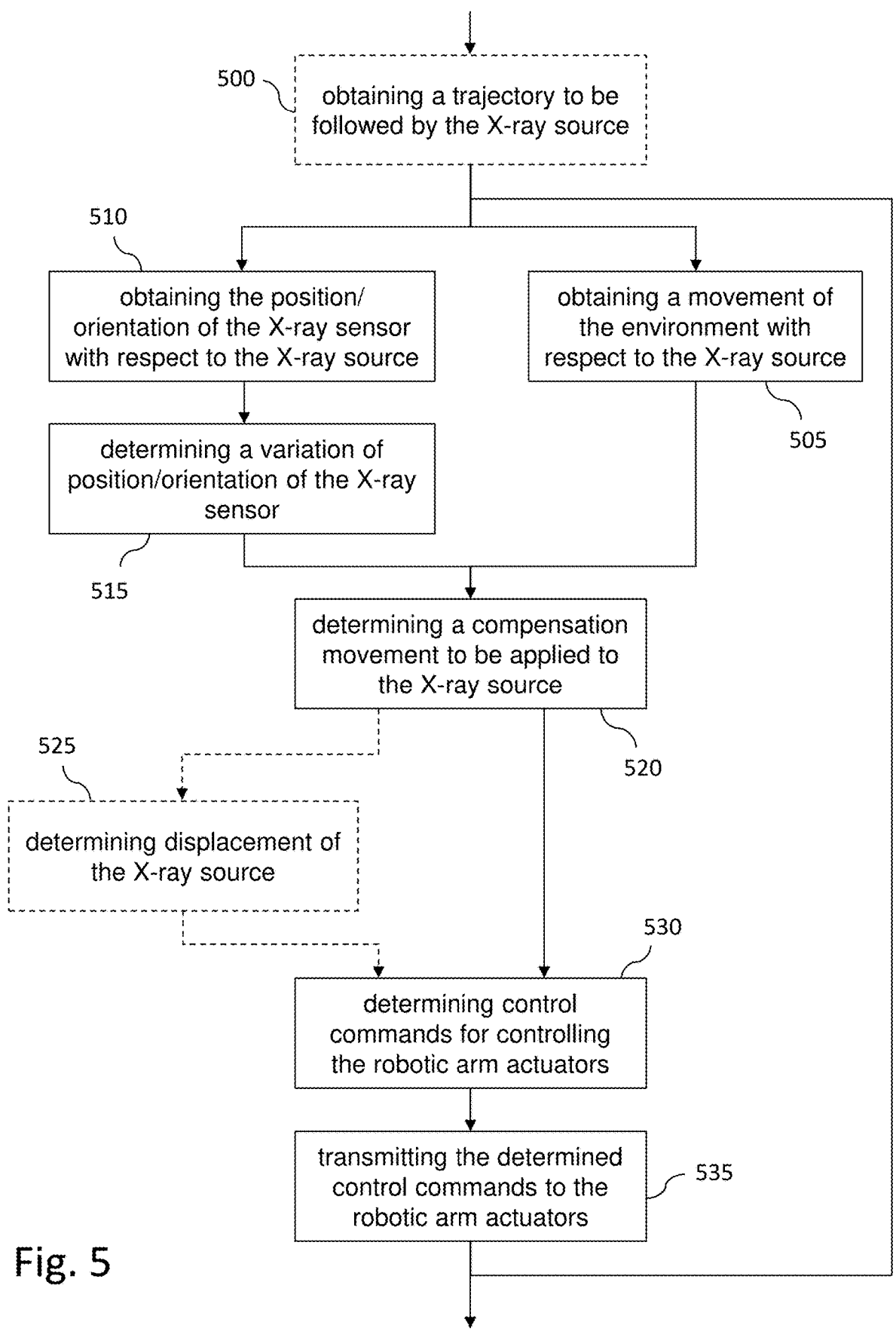
FIG. 5 is a flow chart illustrating an example of steps of a process for controlling the position and/or orientation of a X-ray source according to some embodiments of the invention.

FIG. 5 is a flow chart illustrating an example of steps of a process for controlling the position and/or orientation of an X-ray source according to some embodiments of the invention. These steps may be carried out in the driving unit described above.

As illustrated, a first optional step is directed to obtaining a trajectory to be followed by the X-ray source (step 500), if the latter should move according to a predetermined path with respect to the X-ray sensor, for example in the case of computed tomography imaging. Such a step may be part of an initialization step.

Next, a movement or a displacement of the environment where is located the X-ray source with respect to the X-ray source is obtained (step 505), according to a predetermined reference frame associated with the X-ray source. Since step 505 is performed several times (typically periodically), the obtained movement or displacement corresponds preferably to the displacement of the environment with respect to the X-ray source between two consecutive executions of this step.

In parallel, before, or after, the position and/or orientation of the X-ray sensor with respect to the X-ray source is obtained (step 510), according to the predetermined reference frame associated with the X-ray source. This position and/or orientation is compared with a previous position and/or orientation to determine a displacement (step 515). Again, since steps 505 and 510 are performed several times (typically periodically), the determined displacement corresponds preferably to the displacement of the X-ray sensor, with respect to the X-ray source, between two consecutive executions of these steps.

Alternatively, the displacement of the X-ray sensor with respect to the X-ray source may be directly obtained from a sensor.

Next, a compensation movement of the X-ray source is determined (step 520). According to particular embodiments, this compensation movement is determined from the sum of the compensation movement obtained from the first position sensor and of the compensation movement obtained from the second position sensor. It may be equal to the negative of this sum.

If the X-ray source should move with respect to the X-ray sensor, for example in the case of computed tomography imaging, the displacement of the X-ray source is determined (step 525). This determination is based on the obtained trajectory and on timing information.

Next, control commands are determined for controlling actuators of the robotic arm such as actuators of an actuatable scissor arm and actuators of one or several rotatable, actuatable joints so as to move the X-ray source according to the determined compensation movement and, if applicable, according to the determined displacement along the obtained trajectory (step 530). After being determined, the control commands are transmitted to the actuators to actually move the X-ray source (step 535).

As illustrated, the process is repeated until it becomes unnecessary to compensate for displacement of the X-ray source, for example until the desired images of the tooth or teeth are obtained.

Advantageously, the intraoral X-ray system of the present invention makes installation simpler on a wall of a practitioner's office because the movable components of the intraoral X-ray system can be moved to compensate for defects in the flatness of the wall or for the wall not being sufficiently perpendicular to the floor. Also, due at least in part to its monitoring and compensation capabilities, the intraoral X-ray system can compensate for drift in the position of the X-ray source before and during X-ray imaging, thereby avoiding the need for the taking of additional X-ray images and exposing the patient unnecessarily to extra X-ray dose. The intraoral X-ray system can also, as described herein, compensate automatically for patient movements before and during X-ray imaging. And, because the X-ray source may be precisely moved under the control of the data/signal processing unit along a pre-determined trajectory, the intraoral X-ray system may be used to perform computed tomosynthesis examinations of a patient. Further, because the X-ray source and robotic arm are designed for the X-ray source to be attachable/detachable from the robotic arm and remainder of the intraoral X-ray system, no violent, unstable reaction occurs when the X-ray source is detached and removed from connection with the robotic arm. Instead, the data/signal processing unit detects the variation in weight at the second end of the robotic arm due to removal of the X-ray source and operates the robotic arm and other movable components of the intraoral X-ray system to automatically compensate for the variation in weight in a safe and predictable manner.

Figure 6:
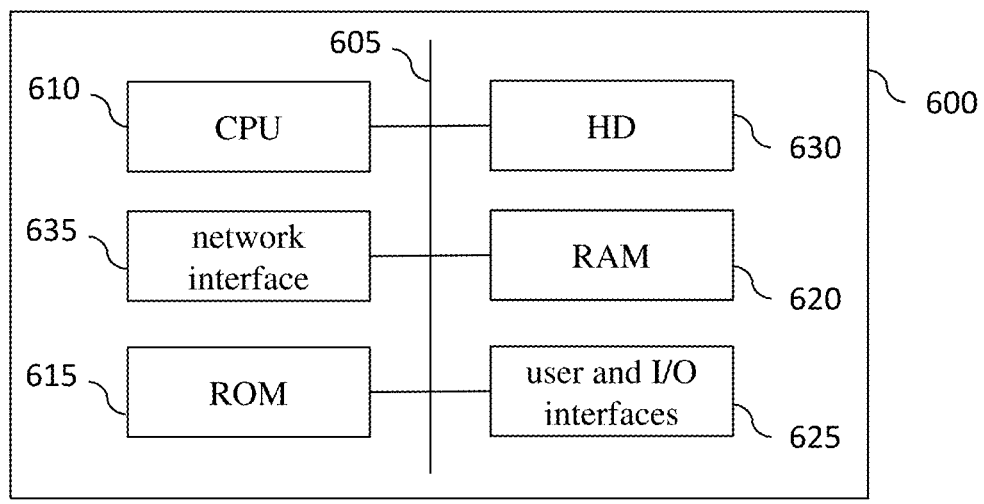
FIG. 6 schematically illustrates a processing device configured to implement at least one embodiment of the present invention.

FIG. 6 schematically illustrates a processing device 600 configured to implement at least some steps of some embodiments of the method according to the present invention, for example steps described by reference to FIG. 5. The processing device 600 may be a device such as a microcomputer, a workstation or a light portable device. The device 600 comprises a communication bus 605 connected to:

a central processing unit 610, such as a microprocessor, denoted CPU;

a read only memory 615, denoted ROM, for storing computer programs for implementing the invention;

a random access memory 620, denoted RAM, for storing the executable code of some steps of some embodiments of the method according to the present invention as well as the registers adapted to record variables and parameters necessary for implementing these steps; and an input/output interface 625 connected to sensors for acquiring position and/or orientation information relative to the X-ray sensor and connected to actuators of the robotic arm.

Optionally, the apparatus 600 may also include the following components:

a data storage means 630 such as a hard disk, for storing computer programs for implementing some steps of some embodiments of the method according to the present invention and data used or produced during the implementation of these steps;

a network interface (×35) to receive or to transmit data over a communication network;

a screen (not represented) for displaying data and/or serving as a graphical interface with the user, by means of a keyboard or any other pointing means, enabling a user to interact with the X-ray system.

The communication bus provides communication and interoperability between the various members included in the apparatus 600 or connected to it. The representation of the bus is not limiting and in particular the central processing unit is operable to communicate instructions to any member of the apparatus 600 directly or by means of another member of the apparatus 600.

The executable code may be stored either in read only memory 615, in the hard disk 630, or in a removable digital medium such as for example a memory card (not represented). According to a variant, the executable code of the programs can be received by means of the communication network, via the network interface 635, in order to be stored in one of the storage means of the apparatus 600 before being executed, such as the hard disk 630.

The central processing unit 610 is adapted to control and direct the execution of the instructions or portions of software code of the program or programs according to the invention, which instructions are stored in one of the aforementioned storage means. On powering up, the program or programs that are stored in a non-volatile memory, for example in the hard disk 630 or in the read only memory 615, are transferred into the random access memory 620, which then contains the executable code of the program or programs, as well as registers for storing the variables and parameters necessary for implementing the invention.

In this embodiment, the apparatus is a programmable apparatus which uses software to implement the invention. However, alternatively, the present invention may be implemented in hardware (for example, in the form of an Application Specific Integrated Circuit or ASIC).

Although the present invention has been described hereinabove with reference to specific embodiments, the present invention is not limited to the specific embodiments, and modifications will be apparent to a person skilled in the art which lie within the scope of the present invention.

Many further modifications and variations will suggest themselves to those versed in the art upon making reference to the foregoing illustrative embodiments, which are given by way of example only and which are not intended to limit the scope of the invention, that being determined solely by the appended claims. In particular, the different features from different embodiments may be interchanged, where appropriate.

In the claims, the word "comprising" does not exclude other elements or steps, and the indefinite article "a" or "an" does not exclude a plurality. The mere fact that different features are recited in mutually different dependent claims does not indicate that a combination of these features cannot be advantageously used.

The invention claimed is:

1. An intraoral X-ray system, the system comprising:
    an X-ray source located in an environment;
    a robotic arm comprising an actuatable scissor arm, the robotic arm having a first end configured to be attached to a mounting and a second end attached to the X-ray source, at least one of the first and the second end comprising a rotatable actuatable joint;
    a position sensor to determine variation of position and/or orientation of the environment with respect to the X-ray source and variation of position and/or orientation of a mobile X-ray sensor with respect to the X-ray source; and
    a driving unit actuating the robotic arm as a function of the determined variation of position and/or orientation to control the position and/or orientation of the X-ray source with respect to a predetermined position and/or orientation of the X-ray source.

2. The system according to claim 1, wherein the variation of position and/or orientation of the environment with respect to the X-ray source and the variation of position and/or orientation of the mobile X-ray sensor with respect to the X-ray source are determined within a same reference frame associated with the X-ray source.

3. The system according to claim 1, wherein the driving unit is configured to control the actuatable scissor arm and/or at least one of the rotatable actuatable joints.

4. The system according to claim 3, wherein the driving unit is configured to lock the actuatable scissor arm and/or at least one of the rotatable actuatable joints in a predetermined position.

5. The system according to claim 1, wherein the position sensor comprises a first position sensor for determining variation of position and/or orientation of the environment with respect to the X-ray source and a second position sensor for determining variation of position and/or orientation of a mobile X-ray sensor with respect to the X-ray source, each of the first and the second position sensor comprising at least one of a gyroscope, an accelerometer, and a localizer for locating a predetermined member.

6. The system according to claim 5, wherein the localizer comprises a radio receiver and a computing unit for locating at least one radio emitter.

7. The system according to claim 5, wherein the localizer comprises at least two cameras and a computing unit configured for locating a spatial arrangement of visual markers, and wherein the visual markers are located on the X-ray sensor and are in the field of view of the cameras.

8. The system according to claim 1, wherein each of the rotatable actuatable joints enables a rotation about one axis, two axes, or three axes.

9. The system according to claim 1, wherein the driving unit is configured to control a movement of the X-ray source according to a predetermined path with respect to the X-ray sensor.

10. The system according to claim 1, wherein the X-ray source is detachable from the second end of the robotic arm.

11. The system according to claim 10, wherein the X-ray source is controlled and powered through a connector comprising a first part belonging to the robotic arm and a second part belonging to the X-ray source, the second part of the connector making it possible to connect an external power module to the X-ray source to provide power to the X-ray source.

12. The system according to claim 10, wherein the X-ray source comprises a display.

13. The system according to claim 1, wherein the system further comprises an X-ray sensor.

14. The system according to claim 13, wherein the system further comprises at least one radio emitter carried by the X-ray sensor.

15. The system according to claim 1, wherein the driving unit is configured to actuate the robotic arm to control the position and/or orientation of the X-ray source with respect to the X-ray sensor during one of an approach stage prior to acquisition, an acquisition stage, or a storage stage further to acquisition.

16. The system according to claim 15, wherein the system further comprises an obstacle detector, and wherein the driving unit is configured for stopping movement of the X-ray source upon detection of an obstacle on a trajectory of the X-ray source.

17. A method for controlling an X-ray system, the method comprising the steps of:
    obtaining a variation of a position and/or an orientation of the environment where an X-ray source is located with respect to an X-ray source and a variation of a position and/or an orientation of the X-ray sensor with respect to the X-ray source;
    determining in real-time a movement of the X-ray source to compensate for the obtained variations of position and/or orientation; and
    actuating the robotic arm to move the X-ray source as a function of the determined movement.

18. The method according to claim 17, wherein determining in real-time the movement of the X-ray source comprises determining in real-time a compensation movement of the X-ray source to compensate for the obtained variations of position and/or orientation of the X-ray source and/or of the X-ray sensor and obtaining a position to reach along a predetermined path to be followed by the X-ray source with respect to the X-ray sensor, the determined movement of the X-ray source resulting from the combination of the compensation movement and of the obtained position.

19. A non-transitory computer program product for a programmable apparatus, the computer program product comprising a sequence of instructions for implementing each of the steps of the method according to claim 17 when loaded into and executed by the programmable apparatus.

20. A non-transitory computer-readable storage medium storing instructions of a computer program for implementing each of the steps of the method according to claim 17.

* * * * *